US012642814B2

(12) United States Patent
Cerini

(10) Patent No.: US 12,642,814 B2
(45) Date of Patent: Jun. 2, 2026

(54) TOPICAL ANTIVIRAL COMPOSITIONS COMPRISING HYALURONIC ACID AND CARRAGEENAN

(71) Applicant: RICERFARMA S.R.L., Milan (IT)

(72) Inventor: Roberto Cerini, Albignasego (IT)

(73) Assignee: RICERFARMA S.R.L., Milan (IT)

( * ) Notice: Subject to any disclaimer, the term of this patent is extended or adjusted under 35 U.S.C. 154(b) by 503 days.

(21) Appl. No.: 18/245,658

(22) PCT Filed: Sep. 17, 2021

(86) PCT No.: PCT/IB2021/058491
§ 371 (c)(1),
(2) Date: Mar. 16, 2023

(87) PCT Pub. No.: WO2022/058949
PCT Pub. Date: Mar. 24, 2022

(65) Prior Publication Data
US 2023/0355657 A1 Nov. 9, 2023

(30) Foreign Application Priority Data
Sep. 18, 2020 (IT) ........................ 102020000022042

(51) Int. Cl.
| | |
|---|---|
| *A61K 31/728* | (2006.01) |
| *A61K 9/00* | (2006.01) |
| *A61K 31/375* | (2006.01) |
| *A61K 31/6615* | (2006.01) |
| *A61K 31/731* | (2006.01) |
| *A61P 31/22* | (2006.01) |

(52) U.S. Cl.
CPC .......... *A61K 31/728* (2013.01); *A61K 9/0014* (2013.01); *A61K 9/006* (2013.01); *A61K 31/375* (2013.01); *A61K 31/6615* (2013.01); *A61K 31/731* (2013.01); *A61P 31/22* (2018.01)

(58) Field of Classification Search
None
See application file for complete search history.

(56) References Cited

U.S. PATENT DOCUMENTS

| | | | | |
|---|---|---|---|---|
| 5,658,893 | A | * 8/1997 | Anderson | ............ A61K 31/737 |
| | | | | 514/59 |
| 2009/0068259 | A1 * | 3/2009 | Pilch | ....................... A61P 43/00 |
| | | | | 514/777 |
| 2009/0263473 | A1 * | 10/2009 | Hong | .................... A61K 8/553 |
| | | | | 424/94.1 |
| 2012/0135087 | A1 | 5/2012 | Schiena | |
| 2018/0360702 | A1 * | 12/2018 | Demarcq | ............... A61K 8/922 |

FOREIGN PATENT DOCUMENTS

| | | | | |
|---|---|---|---|---|
| CH | 691030 | | 4/2001 | |
| JP | 2012206946 | A * | 10/2012 | |
| KR | 100853301 | B1 * | 8/2008 | .......... A61K 8/9789 |
| WO | WO-2020146752 | A1 * | 7/2020 | ............. A61P 31/04 |

OTHER PUBLICATIONS

Cermelli C. et al., "In vitro evaluation of antiviral and virucidal activity of a high molecular weight hyaluronic acid", Virology Journal, 2011, 8:141.

De S.F.-Tischer P.C. et al., "Chemical structure and antiviral activity of carrageenans from Meristiella gelidium against herpes simplex and dengue virus", Carbohydrate Polymers 63 (2006) 459-465.

Möller S. et al., "Synthesis and antiherpetic activity of carboxymethylated and sulfated hyaluronan derivatives", Carbohydrate Polymers 90 (2012) 608-615.

Pujol C. A. et al., "Antiviral activity of a carrageenan from Gigartina Skottsbergii against intraperitoneal murine herpes simplex virus infection", Planta Medica, vol. 72, No. 2, Feb. 1, 2006, pp. 121-125.

Search Report and Written Opinion of PCT/IB2021/058491 issued Jan. 7, 2022.

Gonzalez M E et al., "Polysaccharides as antiviral agents: antiviral activity of carrageenan", Antimicrobial Agents and Chemotherapy, Sep. 1987, pp. 1388-1393, vol. 31, No. 9.

Office Action issued Feb. 20, 2026 in connection with counterpart Japanese Patent Application No. 2023-517998.

* cited by examiner

*Primary Examiner* — Dale R Miller

(74) *Attorney, Agent, or Firm* — Silvia Salvadori, P.C.; Silvia Salvadori

(57) ABSTRACT

Disclosed are topical compositions comprising hyaluronic acid or salts thereof and iota-carrageenan, preferably in a mucoadhesive matrix containing ascorbyl palmitate and choline alfoscerate. The compositions according to the invention are useful for topical treatment of Herpesvirus infections.

9 Claims, No Drawings

TOPICAL ANTIVIRAL COMPOSITIONS COMPRISING HYALURONIC ACID AND CARRAGEENAN

This application is a U.S. national stage of PCT/IB2021/058491 filed on 17 Sep. 2021, which claims priority to and the benefit Italian Patent Application No. 102020000022042 filed on 18 Sep. 2020, the contents of which are all incorporated herein by reference in their entireties.

The present invention relates to topical compositions comprising hyaluronic acid or salts thereof and carrageenan, and at least one pharmaceutically acceptable excipient or carrier, which are useful to prevent, inhibit and effectively treat viral infections, in particular those caused by Herpes simplex and papillomavirus, at the same time maintaining and restoring the integrity of the mucosal and epidermal tissue.

PRIOR ART

Carrageenan is a linear sulphated polysaccharide extracted from edible red seaweed, consisting of galactose derivatives arranged in an alternating series of 1,3 and 1,4 bonds.

There are three main varieties of carrageenan, differentiated by their degree of sulphation: kappa-carrageenan, which has one sulphate group per disaccharide, iota-carrageenan, which has two, and lambda-carrageenan, which has three.

Carrageenan is used as an additive (E 407) in the food, cosmetics and pharmaceutical industries, as a gelling agent, thickener and emulsifier.

Scientific evidence demonstrates the ability of carrageenan to inhibit the infectivity of many viruses, including papillomavirus (HPV) and Herpes simplex virus (HSV), which are responsible, for example, for the onset in humans of warts and labial and genital herpes respectively.

There is also scientific evidence of the antiviral action performed by high-molecular-weight hyaluronic acid (HA) against both RNA viruses and DNA viruses, suggesting a non-specific action mechanism involving interaction with the cell membrane structures, preventing the viruses from adhering to specific receptors.

Inhibitory action has been demonstrated, for example, against Coxsackie virus B5, Herpes Simplex Virus-1, Mumps Virus, Adenovirus-5, Influenza Virus A/H1N1, and Human Herpesvirus-6.

The anti-inflammatory and tissue-repair action of high-molecular-weight HA and its sodium salt is also known.

DESCRIPTION OF THE INVENTION

It has surprisingly been found that topical use on damaged mucosa and epidermis of a combination of high-molecular-weight hyaluronic acid and iota-carrageenan, preferably in a bio/mucoadhesive matrix, prevents, inhibits and effectively treats viral infections, in particular those caused by Herpes simplex and papillomavirus, at the same time maintaining and restoring the integrity of the mucosal and epidermal tissue.

Documented scientific evidence exists of the antiviral action exerted by high-molecular-weight HA and carrageenan. A combination of the two substances gives rise to a synergistic antiviral effect with a broader spectrum, which is useful for the manufacture of products with a protective antiviral action.

The invention therefore provides, in a first aspect, topical compositions comprising high-molecular-weight hyaluronic acid or salts thereof and iota-carrageenan, and at least one pharmaceutically acceptable excipient or carrier.

According to a preferred aspect of the invention, the combination of hyaluronic acid and iota-carrageenan is carried in a muco/bioadhesive matrix containing ascorbyl palmitate and choline alfoscerate.

The muco/bio-adhesive matrix can be prepared, for example, with polymers such as glucan, sodium carboxymethyl beta glucan, chitosan, carboxymethyl chitosan, carboxymethylcellulose, hydroxyethylcellulose, carbomer, PVA (polyvinyl alcohol), PVP (polyvinylpyrrolidone), polycarbophil (polyacrylic acid crosslinked with divinyl glycol), PVM/MA copolymer or VP/EICOSENE copolymer.

Hyaluronic acid or a salt thereof, preferably sodium hyaluronate, has an average molecular weight Mw ranging between 800,000 and 4,000,000 Da, and is present in the compositions of the invention at the concentration of 0.0005% to 50.0% w/w, while the percentage of carrageenan ranges between 0.0004 and 5% w/w.

When present, ascorbyl palmitate and choline alfoscerate have concentrations ranging between 0.0004% w/v and 0.050% w/v, and between 0.001% w/v and 5.00% w/v, respectively.

The concentration of ascorbyl palmitate preferably ranges between 0.005% w/v and 0.025% w/v, and that of choline alfoscerate ranges between 0.001% w/v and 0.500% w/v.

The compositions according to the invention are useful for the treatment of viral infections of the skin and mucosa, and in particular for the treatment of labial and genital herpes caused by Herpes simplex virus (HSV1 and HSV2) and for the protective treatment of warts caused by papillomavirus (HPV).

The compositions according to the invention are useful in particular in the prevention and treatment of cutaneous, labial, ocular, nasal, auricular, genital and anal herpes, warts, and inflammatory and/or skin- and mucosa-damaging disorders in general.

Mucosal inflammation and damage here refer to all irritant and tissue-damaging symptoms accompanied by pain and itching and characterised by the appearance, on the skin or mucosa, of clusters of blisters on a reddened base having a viral etiology.

The compositions are suitable for both human and veterinary use.

The antiviral action mechanism of both high-molecular-weight HA and iota-carrageenan does not involve a direct virucidal action but an indirect action attributable to inhibition of adherence of the virus to the specific receptors present on the cells.

The anti-hyaluronidase action represents a further important functional element that increases the anti-inflammatory and tissue-repair efficacy of hyaluronic acid, which is protected against the action of endogenous and bacterial hyaluronidases, thereby ensuring its functional, lengthy residence time in situ and therefore greater efficacy associated with its greater bioavailability and structural integrity.

Moreover, the anti-hyaluronidase action also performs an antibacterial/anti-inflammatory action; many bacteria perform an inflammatory action mediated by specific hyaluronidases which promote tissue colonisation, thereby promoting the onset and spread of infections.

On the basis of the considerations set out above, the anti-inflammatory/tissue repair action of HA is protected and strongly enhanced by the anti-hyaluronidase action and the presence of the film-forming and bio/mucoadhesive matrix able promote tissue protection and repair (wound healing).

The antiviral activity of the compositions according to the invention was evaluated according to the experimental protocol described by Cermelli et al., in Virology Journal 2011, 8:141, "In vitro evaluation of antiviral and virucidal activity of a high molecular weight hyaluronic acid".

The studies were conducted by comparing the antiviral efficacy of the combination of iota-carrageenan and hyaluronic acid with that of formulations in a mucoadhesive matrix containing carrageenan alone or hyaluronic acid alone.

The results demonstrate the synergy between hyaluronic acid and iota-carrageenan.

According to a further aspect, the topical compositions according to the invention can also include further known active ingredients for topical treatment of the mucosa, such as those described in Martindale, The Complete Drug Reference, 34th Edition.

The compositions according to the invention can be formulated in a way suitable for topical administration, and can be prepared by conventional methods, such as those described in Remington, The Science and Practice of Pharmacy, 20th Edition, and as shown detail in example 2.

Known excipients or carriers can also be added to optimise the specific use of the compositions, such as those described in Handbook of Pharmaceutical Excipients, 6th Edition, Pharmaceutical Press, including film-forming agents, for example.

Examples of preferred formulations are gels (hydrogels, lipogels and anhydrous gels), oil in water (o/w) and water-in-oil (w/o) emulsions, creams, ointments, sprays, powders, lotions, foams, solutions and suspensions.

The compositions are most preferably in aqueous gel (hydrogel) form, which can be obtained by using a pharmaceutically acceptable polymer able to absorb a considerable amount of water and thus adhere to the mucosa.

The mucoadhesion of the compositions according to the invention ensures an adequate residence time on the mucosa, which is subject to the leaching action of physical and mechanical factors that can reduce the residence time of the active ingredient, for example in the case of the oral mucosa.

The examples given below further illustrate the invention.

The percentages are expressed as parts by weight (w/w) of the total weight of the composition.

Example 1—Mucoadhesive Liquid Composition for the Treatment of Oral Herpes

| | |
|---|---|
| Choline alfoscerate | 1.000% |
| Sodium hyaluronate (average MW 1,500,000 Da) | 0.300% |
| Iota-carrageenan | 0.150% |
| Ascorbyl palmitate | 0.005% |
| Polycarbophil | 0.050% |
| Carboxymethyl chitosan | 0.100% |
| PVP (polyvinylpyrrolidone) | 0.500% |
| Solubilising agent | q.s. |
| Preservative | q.s. |
| Flavouring | q.s. |
| Demineralised water | q.s. to 100% |

4

Example 2—Mucoadhesive Gel Composition for the Treatment of Oral, Nasal and Genital Herpes

| | |
|---|---|
| Sodium hyaluronate (average MW 1,500,000 Da) | 0.400% |
| Iota-carrageenan | 0.250% |
| Ascorbyl palmitate | 0.040% |
| Choline alfoscerate | 0.200% |
| Carboxymethylcellulose | 1.000% |
| Polycarbophil | 0.500% |
| PVP (polyvinylpyrrolidone) | 1.000% |
| PVA (polyvinyl alcohol) | 0.500% |
| Xylitol | 7.000% |
| Solubilising agent | q.s. |
| Preservative | q.s. |
| Flavouring | q.s. |
| Demineralised water | q.s. to 100%. |

Preparation Method

Demineralised water, xylitol, polycarbophil, PVP (polyvinylpyrrolidone), PVA (polyvinyl alcohol), iota-carrageenan and ascorbyl palmitate are poured into a turboemulsifier, in sequence, heated to a temperature of 75° C., and left under stirring until a clear, homogeneous mass is obtained. The mass is then is cooled to 65° C., and carboxymethylcellulose and sodium hyaluronate are introduced under stirring in the indicated sequence.

Stirring is continued after each addition until a homogeneous, lump-free gelled mass is obtained.

The mass is maintained under stirring and under vacuum for at least 60 minutes.

Phase A is prepared in a stainless steel container with stirrer, by introducing the solubilising agent, preservative and flavouring in sequence. The mixture is heated to 45° C.±1° C. for 60 minutes, until a clear, homogeneous mass is obtained.

Phase B is prepared in another stainless steel container with stirrer, by adding demineralised water and choline alfoscerate in sequence.

The mixture is maintained under stirring until a homogeneous mass is obtained.

Phase A and phase B are then introduced into the mass contained in the turboemulsifier under stirring and under vacuum.

The resulting mass is maintained under stirring and under vacuum until a homogeneous, lump-free mass is obtained. Cooling then begins, and when the temperature of 30° C. is reached, mixing stops, and the vacuum is slowly relieved with the mixers switched off.

Example 3—Mucoadhesive Gel Composition for the Treatment of Cutaneous and Anogenital Herpes

| | |
|---|---|
| Sodium hyaluronate (average MW 1,500,000 Da) | 0.500% |
| Iota-carrageenan | 0.500% |
| Ascorbyl palmitate | 0.050% |
| Choline alfoscerate | 0.100% |
| Carboxymethylcellulose | 1.000% |
| Polycarbophil | 0.400% |
| Carboxymethyl chitosan | 0.150% |
| PVP (polyvinylpyrrolidone) | 1.500% |
| PVA (polyvinyl alcohol) | 0.500% |
| Xylitol | 7.500% |
| Solubilising agent | q.s. |
| Preservative | q.s. |
| Flavouring | q.s. |
| Demineralised water | q.s. for 100% |

Example 4—Mucoadhesive Liquid Composition for the Treatment of Herpes of the Oral, Nasal and Aural Mucosa

| | |
|---|---|
| Sodium hyaluronan (average MW 1,500,000 Da) | 0.200% |
| Iota-carrageenan | 0.050% |
| Ascorbyl palmitate | 0.020% |
| Choline alfoscerate | 0.050% |
| Polycarbophil | 0.050% |
| Carboxymethyl chitosan | 0.050% |
| PVP (polyvinylpyrrolidone) | 0.200% |
| PVA (polyvinyl alcohol) | 0.100% |
| Xylitol | 7.500% |
| Solubilising agent | q.s. |
| Preservative | q.s. |
| Flavouring | q.s. |
| Demineralised water | q.s. to 100% |

Example 5—Mucoadhesive Gel Composition for Use in Herpes of the Nasal Mucosa

| | |
|---|---|
| Choline alfoscerate | 0.050% |
| Sodium hyaluronate (average MW 1,500,000 Da) | 0.200% |
| Iota-carrageenan | 0.350% |
| Ascorbyl palmitate | 0.020% |
| Carboxymethylcellulose | 4.500% |
| Polycarbophil | 0.300% |
| PVM/MA copolymer | 0.150% |
| PVP (polyvinylpyrrolidone) | 0.500% |
| PVA (polyvinyl alcohol) | 0.100% |
| Distilled Euphrasia water | 10.000% |
| Sodium chloride | 0.800% |
| Dibasic sodium phosphate dodecahydrate | 0.300% |
| Monobasic sodium phosphate monohydrate | 0.030% |
| Solubilising agent | q.s. |
| Preservative | q.s. |
| Demineralised water | q.s. to 100% |

Example 6—Mucoadhesive Liquid Composition for the Treatment of Ocular Herpes

| | |
|---|---|
| Choline alfoscerate | 0.010% |
| Sodium hyaluronate (average MW 1,500,000 Da) | 0.150% |
| Iota-carrageenan | 0.100% |
| Ascorbyl palmitate | 0.005% |
| Polycarbophil | 0.050% |
| Carboxymethyl chitosan | 0.050% |
| Distilled witch hazel water | 10.000% |
| Distilled camomile water | 10.000% |
| Sodium chloride | 0.800% |
| Dibasic sodium phosphate dodecahydrate | 0.300% |
| Monobasic sodium phosphate monohydrate | 0.030% |
| EDTA | 0.050% |
| Demineralised water | q.s. to 100% |

Example 7—Mucoadhesive Liquid Composition for the Treatment of Aural Herpes

| | |
|---|---|
| Choline alfoscerate | 0.100% |
| Sodium hyaluronate (average MW 1,500,000 Da) | 0.100% |
| Iota-carrageenan | 0.200% |
| Ascorbyl palmitate | 0.015% |

-continued

| | |
|---|---|
| Polycarbophil | 0.050% |
| PVM/MA copolymer | 0.150% |
| Glycerol | 50.000% |
| Demineralised water | q.s. to 100% |

Example 8—Mucoadhesive Liquid Composition for Application to the Vaginal and Vulvar Mucosa

| | |
|---|---|
| Choline alfoscerate | 0.050% |
| Sodium hyaluronate (average MW 1,500,000 Da) | 0.250% |
| Iota-carrageenan | 0.500% |
| Ascorbyl palmitate | 0.050% |
| Polycarbophil | 0.100% |
| PVM/MA copolymer | 0.050% |
| PVP (polyvinylpyrrolidone) | 0.200% |
| PVA (polyvinyl alcohol) | 0.100% |
| Sodium chloride | 0.800% |
| Preservative | q.s. |
| Perfume | q.s. |
| Demineralised water | q.s. to 100% |

Example 9—Mucoadhesive Gel for Application to the Vaginal and Vulvar Mucosa

| | |
|---|---|
| Choline alfoscerate | 0.025% |
| Sodium hyaluronate (average MW 1,500,000 Da) | 0.150% |
| Iota-carrageenan | 0.250% |
| Ascorbyl palmitate | 0.040% |
| Carboxymethylcellulose sodium | 4.500% |
| Polycarbophil | 0.250% |
| PVM/MA copolymer | 0.150% |
| PVP (polyvinylpyrrolidone) | 0.500% |
| PVA (polyvinyl alcohol) | 0.100% |
| Sodium chloride | 0.800% |
| Solubilising agent | q.s. |
| Preservative | q.s. |
| Perfume | q.s. |
| Demineralised water | q.s. to 100% |

Example 10—Mucoadhesive Gel for Application to the Mucosa of the Male Genitals

| | |
|---|---|
| Choline alfoscerate | 0.500% |
| Sodium hyaluronate (average MW 1,500,000 Da) | 0.250% |
| Iota-carrageenan | 0.350% |
| Ascorbyl palmitate | 0.050% |
| Carboxymethylcellulose sodium | 4.500% |
| Polycarbophil | 0.250% |
| PVM/MA copolymer | 0.150% |
| PVP (polyvinylpyrrolidone) | 0.500% |
| PVA (polyvinyl alcohol) | 0.100% |
| Sodium chloride | 0.800% |
| Solubilising agent | q.s. |
| Preservative | q.s. |
| Demineralised water | q.s. to 100% |

Example 11—Mucoadhesive Gel for Application to the Anorectal Mucosa

| | |
|---|---|
| Choline alfoscerate | 0.500% |
| Sodium hyaluronate (average MW 1,500,000 Da) | 0.250% |
| Iota-carrageenan | 0.300% |
| Ascorbyl palmitate | 0.015% |
| Carboxymethylcellulose sodium | 4.500% |
| Polycarbophil | 0.250% |
| Carboxymethyl chitosan | 0.150% |
| PVM/MA copolymer | 0.150% |
| PVP (polyvinylpyrrolidone) | 0.500% |
| PVA (polyvinyl alcohol) | 0.100% |
| Distilled white thyme water | 10.000% |
| Distilled lavender water | 10.000% |
| Distilled cornflower water | 10.000% |
| Sodium chloride | 0.800% |
| Solubilising agent | q.s. |
| Preservative | q.s. |
| Demineralised water | q.s. to 100% |

Example 12—Mucoadhesive O/W Emulsion for the Treatment of Cutaneous, Genital, Vulvo-Vaginal and Anorectal Herpes

| | |
|---|---|
| Choline alfoscerate | 0.200% |
| Sodium hyaluronate (average MW 1,500,000 Da) | 0.250% |
| Iota-carrageenan | 0.500% |
| Ascorbyl palmitate | 0.010% |
| Hydrogenated polyisobutene | 6.000% |
| C15-19 alkane | 3.000% |
| Cetearyl alcohol | 3.000% |
| C20-22 alkyl phosphate | 2.750% |
| C20-22 alcohol | 2.250% |
| Betaine | 1.000% |
| Ethyl stearate | 1.000% |
| Choline alfoscerate | 0.500 |
| Hydroxyethyl acrylate/acryloyl dimethyl taurate copolymer | 0.375% |
| Squalane | 0.255% |
| Polycarbophil | 0.100% |
| PVP (polyvinylpyrrolidone) | 0.100% |
| PVA (polyvinyl alcohol) | 0.100% |
| PVM/MA copolymer | 0.050% |
| Preservative | q.s |
| Perfume | q.s |
| Solubilising agent | q.s |
| Stabilisers | q.s |
| Demineralised water | q.s. to 100% |

Example 13—Mucoadhesive Composition for the Treatment of Genital Herpes in the Form of a Vaginal Pessary

| | |
|---|---|
| Choline alfoscerate | 0.100% |
| Sodium hyaluronate (average MW 1,500,000 Da) | 0.200% |
| Iota-carrageenan | 1.000% |

-continued

| | |
|---|---|
| Ascorbyl palmitate | 0.045% |
| Carboxymethyl chitosan | 0.050% |
| Carboxymethyl beta glucan | 0.050% |
| Gelatin | 20.000% |
| Glycerol | 70.000% |
| Demineralised water | q.s. to 100% |

Example 14—Mucoadhesive Composition for the Treatment of Anorectal Herpes for Anorectal Application in an Enema

| | |
|---|---|
| Choline alfoscerate | 0.300% |
| Sodium hyaluronate (average MW 1,500,000 Da) | 0.300% |
| Iota-carrageenan | 0.500% |
| Ascorbyl palmitate | 0.050% |
| Colloidal silicon dioxide | 1.700% |
| Polyvinylpyrrolidone | 0.840% |
| Carboxymethylcellulose | 0.840% |
| Polycarbophil | 0.100% |
| Carboxymethyl chitosan | 0.050% |
| Sodium benzoate | 0.400% |
| Potassium metabisulphite | 0.250% |
| Phosphoric acid | 0.100% |
| Demineralised water | q.s. to 100% |

The invention claimed is:

1. Method of treating viral infections caused by Herpesvirus in a subject in need thereof with a composition comprising hyaluronic acid or salts thereof and iota-carrageenan, and at least one pharmaceutically acceptable excipient or carrier, said method comprising
administering to said subject a pharmaceutically effective amount of said composition.

2. The method according to claim 1, wherein said composition further contain
ascorbyl palmitate and choline alfoscerate.

3. The method according to claim 1, wherein the pharmaceutically acceptable carrier is a mucoadhesive matrix.

4. The method according to claim 1, wherein hyaluronic acid or salt thereof has an average molecular weight Mw ranging between 800,000 and 4,000,000 Da.

5. The method according to claim 4, wherein said salt of hyaluronic acid is sodium hyaluronate.

6. The method according to claim 1, wherein the iota-carrageenan concentration ranges between 0.0004 and 5.000% w/w.

7. The method according to claim 2, wherein the ascorbyl palmitate concentration ranges between 0.0004% and 0.050% w/v.

8. The method according to claim 2, wherein the choline alfoscerate concentration ranges between 0.001% w/v and 5.00% w/v.

9. The method according to claim 1, wherein the compositions is in the form of hydrogels, lipogels, anhydrous gels, O/W and W/O emulsions, solutions or suspensions.

* * * * *